(12) United States Patent
Kvassheim

(10) Patent No.: US 6,965,430 B2
(45) Date of Patent: Nov. 15, 2005

(54) DEVICE FOR A TRANSPARENT PIPE INTENDED FOR OPTICAL COUNTING AND MEASURING

(76) Inventor: Torbjørn Kvassheim, Gosenstien 1, Hafrsfjord (NO) N-4041

( * ) Notice: Subject to any disclaimer, the term of this patent is extended or adjusted under 35 U.S.C. 154(b) by 62 days.

(21) Appl. No.: 10/473,243

(22) PCT Filed: Mar. 22, 2002

(86) PCT No.: PCT/NO02/00119

§ 371 (c)(1),
(2), (4) Date: Sep. 25, 2003

(87) PCT Pub. No.: WO02/079721

PCT Pub. Date: Oct. 10, 2002

(65) Prior Publication Data

US 2004/0080745 A1    Apr. 29, 2004

(30) Foreign Application Priority Data

Mar. 29, 2001 (NO) .................................. 20011619

(51) Int. Cl.[7] .......................................... G01N 21/05
(52) U.S. Cl. ................................................. 356/246
(58) Field of Search ................. 356/234, 28, 336–339; 73/54.04–54.09; 250/574–576, 373, 461.2

(56) References Cited

U.S. PATENT DOCUMENTS

| | | | |
|---|---|---|---|
| 5,264,906 A * | 11/1993 | Ferer et al. | 356/28 |
| 5,426,501 A | 6/1995 | Hokanson et al. | |
| 5,584,982 A * | 12/1996 | Dovichi et al. | 204/603 |
| 5,946,093 A * | 8/1999 | DeFreez et al. | 356/339 |
| 6,561,010 B2 * | 5/2003 | Wilson et al. | 73/54.04 |

FOREIGN PATENT DOCUMENTS

| | | |
|---|---|---|
| EP | 0 556 748 | 8/1993 |
| FR | 2 634 573 | 1/1990 |

* cited by examiner

Primary Examiner—Tu T. Nguyen
(74) Attorney, Agent, or Firm—Andrus, Sceales, Starke & Sawall, LLP

(57) ABSTRACT

A circular, transparent pipe device for optically counting and measuring objects carried with a fluid within the pipe by means of light beams exiting through the wall of the pipe. The outer radius of the pipe equals or nearly equals the product of the inner radius of the pipe (1) and the ratio of the light refraction index of the fluid within the pipe to the light refraction index of the medium surrounding the pipe. A camera or other apparatus is located at a camera point at a mean distance from the pipe between distal and proximal points of intersection of light beams hitting the internal wall of the pipe to sense the light beams.

3 Claims, 1 Drawing Sheet

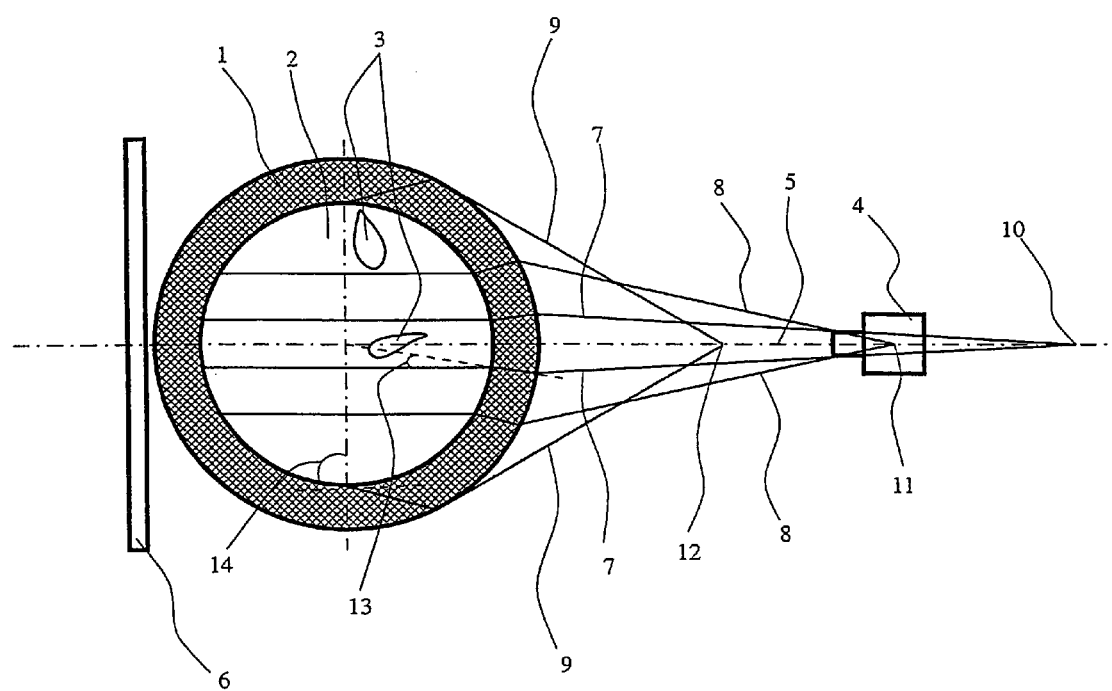

DEVICE FOR A TRANSPARENT PIPE INTENDED FOR OPTICAL COUNTING AND MEASURING

CROSS REFERENCE TO RELATED APPLICATION

The present application is the U.S. national stage application of International Application PCT/NO02/00119, filed Mar. 22, 2002, which international application was published on Oct. 10, 2002 as International Publication WO 02/079721. The International Application claims priority of Norwegian Patent Application 20011619, filed Mar. 29, 2001.

FIELD OF THE INVENTION

The invention relates to a device for a transparent pipe, arranged to allow observation, counting or measuring of objects carried through the pipe by a fluid.

BACKGROUND OF THE INVENTION

The invention was made in connection with the counting and measuring of fish carried with water within a pipe, the counting and measuring being carried out by means of an optical apparatus which comprises a camera and is connected to a computer for analysing camera images. The present description is essentially directed towards this field of application, without the intention of being limiting. The counting/measuring apparatus as such is not part of the invention.

It is known to provide windows in a pipe wall to allow counting and measuring of objects passing. It is often preferred to mount a transparent pipe section in the pipe because that facilitates observation from several sides and because it makes it easier to have the necessary light where liquid and objects are to be observed.

Light refraction leads to the distortion of objects within the pipe when they are observed from the outside, and this is destructive to optical measuring, for example the measuring of the area of the objects or pattern recognition.

In particular, regions next to the centre line of the pipe are subject to distortion.

To avoid said distortion, it is common to use a transparent pipe section with at least one plane transparent side, through which the objects may be observed; typically a rectangular pipe section is used.

There are several drawbacks to mounting a rectangular pipe section to an ordinary circular pipe. A transition between a round and a rectangular cross-section increases the costs, and the dimensions of the pipe section will be unduly large. Further, turbulence or air pockets are apt to occur, interfering with the measurements.

SUMMARY OF THE INVENTION

The object of the invention is to provide a transparent pipe section of a circular cross-section for observation, counting and measuring of items carried through the pipe section, in which the optical distortion is also reduced.

The object is achieved through features as specified in the following description and subsequent claims.

According to the invention a circular transparent pipe is used, in which the material thickness of the pipe is such that a light beam directed across the pipe and tangent to the internal wall of the pipe, is totally reflected when the light beam hits the outer surface of the pipe. This means that a light beam which is tangent to the internal wall of the pipe, is refracted in such a way that it is also tangent to the outer wall of the pipe. Given the internal radius r of the pipe, the light refraction index $n_1$ of fluid in the pipe and the light refraction index $n_2$ of the medium externally to the pipe, the external radius R of the pipe may be calculated through the formula $R=r*n_1/n_2$ and the material thickness $t=R-r=r(n_1/n_2-1)$.

The light refraction index is approximately 1.33 of water and about 1 of air. For a transparent pipe carrying water and being surrounded by air, $R=r*1.33$ and the material thickness $t=r*0.33$. This relationship is independent of the light refraction index of the pipe material. The material thickness appearing in this way, is greater than what is normally required for strength considerations in e.g. an apparatus for counting fish.

The wall of a pipe sized according to the invention, refracts light beams which are parallel within the pipe in a plane transverse to the pipe, in towards an optical axis in said plane. The refraction varies with the distance from the optical axis and in such a way that light beams the farthest from the optical axis have the greatest refraction and intersect the optical axis closer to the pipe than light beams closer to the optical axis. A light beam following the optical axis is not refracted.

A camera or other optical apparatus for registering, measuring or counting objects passing in the pipe, may be placed at a camera point about midway between the extreme points, wherein light beams that are parallel within the pipe, intersect the optical axis after being refracted in connection with the pipe wall. Experiments with a line scan camera have shown surprisingly good results when measuring shadow areas on objects illuminated from the opposite side of the pipe. Depending on the camera and optics it may be necessary to proceed tentatively to the best camera location in the proximity of said camera point. The light refraction index of the pipe material will be of influence.

BRIEF DESCRIPTION OF THE DRAWINGS

The invention will be described in detail in the following by means of an exemplary embodiment, and reference is made to the appended drawing showing a cross-section of a transparent pipe with a camera and a light source on diametrically opposite sides of the pipe.

DETAILED DESCRIPTION OF THE INVENTION

In the FIGURE the reference numeral 1 identifies a circular pipe of a transparent material, such as glass, acryl or polycarbonate. In the pipe 1 water 2 is flowing, carrying objects 3 past a camera 4 which is directed towards the pipe 1, so that the optical axis 5 of the camera lens is perpendicular to the pipe 1 and passes through the centre of the pipe 1. A light source 6 is placed, relative to the camera 4, on the diametrically opposite side of the pipe 1, so that the camera may be used to measure the shadow area of the objects 3.

The equipment is surrounded by air.

Three pairs of light beams 7, 8 and 9, the light beams of one pair being on opposite sides of the optical axis 5, show light refraction for parallel light beams within the pipe at a short, mean and maximum distance, respectively, from the optical axis 5. The course of the light beams may be calculated by means of the formula of Snell's law of refraction which is well-known to a person skilled in the art.

According to the invention, the material thickness of the pipe 1 is selected to be such that the light beam 9 is tangent to the internal and external walls of the pipe 1, as explained earlier.

The light beams 7 are refracted and intersect at a point of intersection 10, a long distance from the pipe 1. The light beams 8 intersect at a point of intersection 11, where the camera 4 is located, about midway between the point of intersection 10 and a point of intersection 12, where the light beams 9 intersect one another.

In an experiment, in which the pipe 1 was made of acryl with a light refraction index of 1.49, and the pipe had an internal radius of 175 millimeters and a material thickness of 58 millimeters, the point of intersection 10 was about 820 millimeters from the external wall of the pipe 1, whereas the distance to the point 12 was about 440 millimeters. A camera point, the point of intersection 11, at a distance of about 600 millimeters from the pipe 1, gave good shadow area measuring results for objects 3 in an arrangement as shown in the FIGURE.

The point of intersection 10 of the light beams 7 then applied to light beams that hit the internal wall of the pipe at an angle of about 5 angular degrees relative to the axis of incidence, whereas a corresponding angle of the light beams 9 was then 90 angular degrees. The two angles are shown with reference numerals 13 and 14 in FIG. 1. The camera point refers to the focal point of the camera.

The light source 6 is elongate and arranged to provide diffuse light. The light source 6 comprises a standard fluorescent tube covered by a white transparent plate which is not shown. The distance between the pipe 1 and the light source 6 may be substantially shorter than the distance between the pipe 1 and the camera point 11. In the experiment mentioned the shortest distance between the pipe 1 and the light source 6 was about 20 millimeters.

The inner and outer walls of the pipe 1 should be designed with smooth surfaces, so that no scratches or other irregularities will interfere with the light beams. If the camera 4 is a line scan camera, the pipe 1 may have a relatively small length, so that in practice the pipe 1 forms a ring.

What is claimed is:

1. A transparent pipe device of circular cross-section for the optical counting and measuring of objects carried with a fluid within the pipe, wherein light beams exiting through the wall of the pipe are sensed by an optical apparatus, and wherein the pipe comprises one in which the outer radius of the pipe equals or nearly equals the product of the inner radius of the pipe and the ratio of the light refraction index of the fluid within the pipe to the light refraction index of the medium surrounding the pipe.

2. A device according to claim 1 wherein the optical apparatus is placed at a camera point at a mean distance from the pipe between a distal point of intersection of light beams hitting the internal wall of the pipe at an angle of about five angular degrees, and a proximal point of intersection of light beams hitting the internal wall of the pipe at an angle of about ninety angular degrees relative to the axis of incidence.

3. A device according to claim 1 wherein a light source is placed on the diametrically opposite side of the pipe from said optical apparatus and substantially closer to the pipe than the optical apparatus.

* * * * *